United States Patent [19]
Jameson et al.

[11] Patent Number: 6,107,273
[45] Date of Patent: Aug. 22, 2000

[54] TUMOR NECROSIS FACTOR INHIBITORS

[75] Inventors: Bradford A. Jameson, Philadelphia, Pa.; Mariadele Noe, Haddonfield, N.J.

[73] Assignee: Thomas Jefferson University, Philadelphia, Pa.

[21] Appl. No.: 08/377,781

[22] Filed: Jan. 24, 1995

[51] Int. Cl.$^7$ .............................. A61K 38/12; C07K 5/12
[52] U.S. Cl. .................................. 514/9; 514/11; 514/12; 514/13; 514/14; 514/16; 530/317; 530/326; 530/327; 530/328; 530/330
[58] Field of Search ...................................... 530/327, 328, 530/330, 317, 326; 514/14, 16, 9, 12, 13, 11

[56] References Cited

FOREIGN PATENT DOCUMENTS

| | | |
|---|---|---|
| 3841761 | 12/1988 | Germany. |
| 3841761 | 6/1990 | Germany. |
| WO 90/06943 | 6/1990 | WIPO. |
| 9117180 | 11/1991 | WIPO. |
| 9301211 | 1/1993 | WIPO. |

OTHER PUBLICATIONS

File Caplus on STN. No. 119:6744. McDonnell et al. ImmunoMethods, vol. 1, No. 1, pp. 33–39. (abstract and registry No.), 1993.
File Caplus on STN. No. 74:23122. Hiskey et al. J. Org. Chem. vol. 36, No. 1, A. (abstract and registry No.), 1971.
File Caplus on STN. No. 117:192349. Bhatnatger et al. WO 92/09625, Jun. 11, 1992. (abstract and registry No.).
Chemical Abstract No. 1992:572120 on STN. Boehm et al. 'Preparation of Tumor Necrosis Factor Agonists and Antagonists', DE–3841761, Jun. 13, 1990, Abstract and Structure Query, 1992.
Bajusz, S. 'Significance of D–Amino–Acid Residues in Biologically Active Peptides', Pharmazie, 34, 5/6 1979.
Rudinger, J 'Characteristics of amino acids as components of peptide hormones sequence' in Peptide Hormones, (ed. J.A. Parsons). University Park Press, Baltimore, pp. 1–7, 1976.
Sugihara et al. 'Studies on Cyclic Petides. 5. Conformation and Interaction With Small Molecules of Cyclic Hexapeptides Containing Glutamic Acid or Aspartic Acid Residues', J. Org. Chem. vol. 41, No. 15, pp. 2584–2590. (1976).
Aderka et al., "Stabilization of The Bioactivity of Tumor Necrosis Factor by Its Soluble Receptors", J. Exp. Med. 175: 323–329 (1992).
Beutler, Bruce and Cerami, Anthony, "The Biology of Cachectin/TNF—A Primary Mediator of The Host Response" Ann. Rev. Immunol. 1989 7:625–655.
Camussi et al., "Tumor Necrosis Factor/Cachetin Stimulates Peritoneal Macrophages, Polymorphonuclear Neutrophils, and Vascular Endothelial Cells to Synthesize and Release Platelet–Activating Factor" J. Exp. Med. 166: 1390–1404 (1987).
Carswell, E.A. et al., "An Endotoxin–Induced Serum Factor That Causes Necrosis of Tumors", Proc. Natl. Acad. Sci. USA 72: 3666–3670 (1975).

Cerami, Anthony and Beutler, Bruce, "The role of cachectin/TNF in endotoxic shock and cachexia" Immunol. Today 1988 9, 28–31.
Debets, Joop M.H. et al., "The Role of Tumor Necrosis Factor/Cachectin in Septic Shock", Second Vienna Shock Forum: 463–466 (1989).
Fiers, W., "Tumor Necrosis Factor", Febs Letters 1991 285, 199–212.
Goeddel, D.V. et al., "Tumor Necrosis Factors: Gene Structure and Biological Activities" Cold Spring Harbor Symposia on Quantitative Biology 1986 LI, 597–609.
Kern, K.A. and Norton, J.A., "Cancer Cachexia", J. of Parenteral and Enteral Nutrition 1988, 12(3), 286–298.
Kornbluth, R.S. and Edgington, T.S., "Tumor necrosis factor production by human moncytes is a regulated event: induction of TNF–a–Mediated cellular cytotoxicity by endotoxin", J. of Immunology 1986, 137(8), 2585–2591.
Kriegler, M. et al., A novel form of TNF/cachectin is a cell surface cytotoxic transmembrane protein: ramifications for the complex physiology of TNF, Cell 1988, 53, 45–53.
Merrifield, R.B., "Solid Phase Peptide Synthesis. I. The Synthesis of a Tetrapeptide", J. Am. Chem. Soc., 1963, 85, 2149–2154.
Michie, H.R. et al., "Tumour Necrosis Factor and Bacterial Sepsis" Br. J. Surg. 1989 76, 670–671.
Michie, Hamish R., et al., "Detection of Circulating Tumor Necrosis Factor After Endotoxin Administration" New Eng. J. of Med. 1988 318, 1481–1486.
Michie, Hamish R., et al., "Tumor Necrosis Factor and Endotoxin Induce Similar Metabolic Responses in Human Beings" Surgery 1988 104, 280–286.
Michie, Hamish R., et al., "Chronic TNF Infusion Causes Anorexia but Not Accelerated Nitrogen Loss" Ann. Surg. 1989 209, 19–24.
Oliff, A., "The role of tumor necrosis factor (cachectin) in cachexia", Cell 1988, 54, 141–142.
Oliff, A. et al., "Tumors secreting human TNF/cachectin induce cachexia in mice", Cell 1987, 50, 555–563.
Piguet et al., "Tumor necrosis factor/cachectin is an effector of skin and gut lesions of the acute phase of graft–vs.–host disease", J. Exp. Med. 166:1280–1289.

(List continued on next page.)

Primary Examiner—Christopher S. F. Low
Assistant Examiner—Anish Gupta
Attorney, Agent, or Firm—Woodcock Washburn Kurtz Mackiewicz & Norris LLP

[57] ABSTRACT

TNFα antagonist compounds and methods of using the same are disclosed. The compounds comprise a molecular surface that is substantially similar to at least one molecular surface of human TNFα. The compounds bind to TNF receptors but do not produce the same biological effect as that which occurs when TNFα binds to a TNF receptor. Methods of inhibiting tumor necrosis factor activity are disclosed. The methods comprise the step of contacting tumor necrosis factor alpha with a TNFα antagonist. Methods of treating individuals suspected of suffering from or being susceptible to a disease or disorder mediated by tumor necrosis factor-alpha activity are disclosed. The methods comprise the step of administering to said individual a therapeutically effective amount of a TNFα antagonist.

35 Claims, No Drawings

OTHER PUBLICATIONS

Pober et al., "Activation of cultured human endothelial cells by recombinant lymphotoxin: comparison with tumor necrosis factor and interleukin 1 species", The journal of immunology 138:3319–3324 (1987).

Pober et al., "Two distinct monokines, interleukin 1 and tumor necrosis factor, each independently induce biosynthesis and transient expression of the same antigen on the surface of cultured human vascular endothelial cells[1]", The Journal of Immunology, 136 (5) :1680–1687 (1986).

Porteu, F. and Nathan, C., "Shedding of tumor necrosis factor receptors by activated human neutrophils", J. Exp. Med., 172:599–607 (1990).

Pujol–Borrell, Ricardo et al., "HLA class II induction in human islet cells by interferon–γ plus tumor necrosis factor or lymphotoxin", nature, 326:304–306 (1987).

Revhaug, Arthur et al., "Inhibition of Cyclo–oxygenase Attenuates the Metabolic Response to Endotoxin in Humans", *Arch Surg* 1988, 123, 162–170.

Silva, Ayona T. et al., "Prophylactic and Therapeutic Effects of a Monoclonal Antibody to Tumor Necrosis Factor–α in Experimental Gram–Negative Shock" JID 162: 421–427 (1990).

Simpson, Steven Q. et al., "Role of Tumor Necrosis Factor in Sepsis and Acute Lung Injury", *Crit. Care. Clinic* 1989 5, 27–47.

Smith, Richard A., et al., "The Active Form of Tumor Necrosis Factor is a Trimer" J. of Biol. Chem. 1987 262 (15) 6951–6954.

Tracey, Kevin J. et al., "Anti–cachectin/TNF monoclonal antibodies prevent septic shock during lethal bacteraemia", *Nature* 1987, 330(17), 662–664.

Waage, A. et al., "Association between tumour necrosis factor in serum and fatal outcome in patients with meningococcal disease", *The Lancet* 1987, Feb. 14.

Williams, Richard O. et al., "Anti–tumor necrosis factor ameliorates joint disease in murine collagen–induced arthritis", *Proc. Natl. Acad. Sci. USA* 1992, 89, 9784–9788.

```
                         SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:1:

Cys Ala Arg Asp Asn Gln Ala Cys
1               5

(2) INFORMATION FOR SEQ ID NO:2:

(i) SEQUENCE CHARACTERISTICS:
         (A) LENGTH: 9 amino acids
         (B) TYPE: amino acid
         (D) TOPOLOGY: both (ii) MOLECULE TYPE: peptide (xi) SEQUENCE DESCRIPTION: SEQ ID NO:2:

Cys Pro Gln Ala Glu Gly Gln Leu Cys
1               5
```

(2) INFORMATION FOR SEQ ID NO:3:

(i) SEQUENCE CHARACTERISTICS:
        (A) LENGTH: 5 amino acids
        (B) TYPE: amino acid
        (D) TOPOLOGY: both (ii) MOLECULE TYPE: peptide (xi) SEQUENCE DESCRIPTION: SEQ ID NO:3:

```
Pro Arg Glu Thr Pro
1               5
```

(2) INFORMATION FOR SEQ ID NO:4:

(i) SEQUENCE CHARACTERISTICS:
        (A) LENGTH: 4 amino acids
        (B) TYPE: amino acid
        (D) TOPOLOGY: both (ii) MOLECULE TYPE: peptide (xi) SEQUENCE DESCRIPTION: SEQ ID NO:4:

```
Pro Glu Thr Pro
1
```

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: both (ii) MOLECULE TYPE: peptide (xi) SEQUENCE DESCRIPTION: SEQ ID NO:5:

```
Glu Gly Ala Glu
1
```

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: both (ii) MOLECULE TYPE: peptide (ix) FEATURE:
        (A) NAME/KEY: Modified-site
        (B) LOCATION: 3
        (D) OTHER INFORMATION: /note= "Xaa at 3 is Aib"

(xi) SEQUENCE DESCRIPTION: SEQ ID NO:6:

```
Cys Glu Xaa Glu Cys
1               5
```

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: both (ii) MOLECULE TYPE: peptide (ix) FEATURE:
        (A) NAME/KEY: Modified-site
        (B) LOCATION: 1
        (D) OTHER INFORMATION: /note= "Xaa at 1 is penicillamine"

```
        (ix) FEATURE:
              (A) NAME/KEY: Modified-site
              (B) LOCATION: 3
              (D) OTHER INFORMATION: /note= "Xaa at 3 is Aib"

(ix) FEATURE:
              (A) NAME/KEY: Modified-site
              (B) LOCATION: 5
              (D) OTHER INFORMATION: /note= "Xaa at 5 is penicillamine"

(xi) SEQUENCE DESCRIPTION: SEQ ID NO:7:

Xaa Glu Xaa Glu Xaa
1               5

(2) INFORMATION FOR SEQ ID NO:8:

(i) SEQUENCE CHARACTERISTICS:
              (A) LENGTH: 6 amino acids
              (B) TYPE: amino acid
              (D) TOPOLOGY: both (ii) MOLECULE TYPE: peptide (xi) SEQUENCE DESCRIPTION: SEQ ID NO:8:

Cys Glu Gly Ala Glu Cys
1               5

(2) INFORMATION FOR SEQ ID NO:9:

(i) SEQUENCE CHARACTERISTICS:
              (A) LENGTH: 6 amino acids
              (B) TYPE: amino acid
              (D) TOPOLOGY: both (ii) MOLECULE TYPE: peptide (ix) FEATURE:
              (A) NAME/KEY: Modified-site
              (B) LOCATION: 1
              (D) OTHER INFORMATION: /note= "Xaa at 1 is penicillamine"

(ix) FEATURE:
              (A) NAME/KEY: Modified-site
              (B) LOCATION: 6
              (D) OTHER INFORMATION: /note= "Xaa at 6 is penicillamine"

(xi) SEQUENCE DESCRIPTION: SEQ ID NO:9:

Xaa Glu Gly Ala Glu Xaa
1               5

(2) INFORMATION FOR SEQ ID NO:10:

(i) SEQUENCE CHARACTERISTICS:
              (A) LENGTH: 14 amino acids
              (B) TYPE: amino acid
              (D) TOPOLOGY: both (ii) MOLECULE TYPE: peptide (xi) SEQUENCE DESCRIPTION: SEQ ID NO:10:

Cys Pro Arg Glu Thr Pro Glu Gly Ala Glu Ala Lys Pro Cys
1               5                  10

(2) INFORMATION FOR SEQ ID NO:11:

(i) SEQUENCE CHARACTERISTICS:
              (A) LENGTH: 13 amino acids
              (B) TYPE: amino acid
              (D) TOPOLOGY: both
```

(ii) MOLECULE TYPE: peptide (xi) SEQUENCE DESCRIPTION: SEQ ID NO:11:

Cys Pro Glu Thr Pro Glu Gly Ala Glu Ala Lys Pro Cys
1               5                   10

(2) INFORMATION FOR SEQ ID NO:12:

(i) SEQUENCE CHARACTERISTICS:
            (A) LENGTH: 9 amino acids
            (B) TYPE: amino acid
            (D) TOPOLOGY: both (ii) MOLECULE TYPE: peptide (ix) FEATURE:
            (A) NAME/KEY: Modified-site
            (B) LOCATION: 1
            (D) OTHER INFORMATION: /note= "Xaa at 1 is penicillamine"

(ix) FEATURE:
            (A) NAME/KEY: Modified-site
            (B) LOCATION: 9
            (D) OTHER INFORMATION: /note= "Xaa at 9 is penicillamine"

(xi) SEQUENCE DESCRIPTION: SEQ ID NO:12:

Xaa Thr Pro Glu Gly Ala Glu Ala Xaa
1               5

(2) INFORMATION FOR SEQ ID NO:13:

(i) SEQUENCE CHARACTERISTICS:
            (A) LENGTH: 4 amino acids
            (B) TYPE: amino acid
            (D) TOPOLOGY: both (ii) MOLECULE TYPE: peptide (xi) SEQUENCE DESCRIPTION: SEQ ID NO:13:

Arg Ile Ala Val
1

(2) INFORMATION FOR SEQ ID NO:14:

(i) SEQUENCE CHARACTERISTICS:
            (A) LENGTH: 8 amino acids
            (B) TYPE: amino acid
            (D) TOPOLOGY: both (ii) MOLECULE TYPE: peptide (xi) SEQUENCE DESCRIPTION: SEQ ID NO:14:

Cys Ser Tyr Gln Thr Lys Val Cys
1               5

(2) INFORMATION FOR SEQ ID NO:15:

(i) SEQUENCE CHARACTERISTICS:
            (A) LENGTH: 12 amino acids
            (B) TYPE: amino acid
            (D) TOPOLOGY: both (ii) MOLECULE TYPE: peptide (xi) SEQUENCE DESCRIPTION: SEQ ID NO:15:

Cys Arg Ile Ala Val Ser Tyr Gln Thr Lys Val Cys
1               5                   10

(2) INFORMATION FOR SEQ ID NO:16:

```
        (i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:16:

Cys Ser Tyr Gln Thr Lys Cys
1               5

(2) INFORMATION FOR SEQ ID NO:17:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:17:

Cys Ile Ala Val Ser Tyr Gln Thr Lys Cys
1               5                   10

(2) INFORMATION FOR SEQ ID NO:18:

(i) SEQUENCE CHARACTERISTICS:
            (A) LENGTH: 10 amino acids
            (B) TYPE: amino acid
            (D) TOPOLOGY: both (ii) MOLECULE TYPE: peptide (ix) FEATURE:
            (A) NAME/KEY: Modified-site
            (B) LOCATION: 4
            (D) OTHER INFORMATION: /note= "Xaa at 4 is Aib"

(xi) SEQUENCE DESCRIPTION: SEQ ID NO:18:

Cys Ile Ala Xaa Ser Tyr Gln Thr Lys Cys
1               5                   10
```

TUMOR NECROSIS FACTOR INHIBITORS

FIELD OF THE INVENTION

The present invention relates to compounds that inhibit tumor necrosis factor-alpha (TNFα) activity and methods of using such compounds. The present invention relates to compounds that bind to TNF receptors and thereby prevent TNFα from binding to its receptor.

BACKGROUND OF THE INVENTION

The cytokine known as tumor necrosis factor-α (TNFα; also termed cachectin) is a protein secreted primarily by monocytes and macrophages as a soluble homotrimer of 17 kD protein subunits in response to endotoxin or other stimuli (Smith, R. A. et al., *J. Biol. Chem.* 1987, 262, 6951–6954). A membrane-bound 26 kD precursor form of TNFα has also been described (Kriegler, M. et al., *Cell* 1988, 53, 45–53). TNFα was originally discovered in the serum of animals injected sequentially with a bacterial vaccine (bacillus Calmette-Guerin, BCG) and endotoxin (Carswell, E. A. et al., *Proc. Natl. Acad. Sci. USA* 1975, 72, 3666).

The expression of the gene encoding TNFα is not limited to cells of the monocyte/macrophage family. Several human non-monocytic tumor cell lines were shown to produce TNFα. TNFα is also produced by $CD4^+$ and $CD8^+$ peripheral blood T lymphocytes, and by various cultured T and B cell lines.

TNFα plays an integral role in destroying tumors, mediating responses to tissue injury, and protecting hosts from infections by various microorganisms (Goeddel et al., *Cold Spring Harbor Symp. Quant. Biol.* 1986, 51, 597–609; Beutler et al., *Ann. Rev. Immunol.* 1989, 7, 625–655; and, Fiers, FEBS Letters 1991, 285, 199–212). However, its activity appears to be excessive in some disease states and inflammatory reactions such as rheumatoid arthritis, cachexia, and septic shock (Pujol-Borrell et al., *Nature* 1987 326, 304–306; Oliff, *Cell* 1988 54, 141–142; Tracey et al., *Nature* 1987, 330, 662–664). The excess TNFα results in an exaggerated immune response exemplified by overstimulation of interleukin-6 and granulocyte/macrophage-colony stimulating factor (GM-CSF) secretion, enhanced cytotoxicity of polymorphonuclear neutrophils, and prolonged expression of cellular adhesion molecules, all of which can have detrimental effects. The benefits of inhibiting TNFα activity during inflammatory reactions in animal models have been demonstrated using neutralizing monoclonal antibodies to TNFα (Tracey et al., *Nature* 1987, 330, 662–664; Silva et al., *J. Infect. Sis.* 1990, 162, 421–427; and Williams et al., *Proc. Natl. Acad. Sci.* 1992, 89, 9784–9788).

The mechanism of action of TNFα is derived from accumulating evidence which indicates that TNFα is a regulatory cytokine with pleiotropic biological activities. These activities include: inhibition of lipoprotein lipase synthesis ("cachectin"), activation of polymorphonuclear leukocytes, inhibition of cell growth or stimulation of cell growth, cytotoxic action on certain transformed cell types, antiviral activity, stimulation of bone resorption, stimulation of collagenase and prostaglandin E2 production, and immunoregulatory actions, including activation of T cells, B cells, monocytes, thymocytes, and stimulation of the cell-surface expression of major histocompatibility complex class I and class II molecules.

TNFα is noted for its pro-inflammatory actions which result in tissue injury, such as induction of procoagulant activity on vascular endothelial cells (Pober, J. S. et al., *J. Immunol.* 1986, 336, 1680), increased adherence of neutrophils and lymphocytes (Pober, J. S. et al., *J. Immunol.* 1987, 138, 3319), and stimulation of the release of platelet activating factor from macrophages, neutrophils and vascular endothelial cells (Camussi, G. et al., *J. Exp. Med.* 1987, 166, 1390).

Recent evidence implicates TNFα in the pathogenesis of many infections (Cerami, A. et al., *Immunol. Today* 1988, 9, 28), immune disorders, neoplastic pathology, e.g., in cachexia accompanying some malignancies (Oliff, A. et al., *Cell* 1987, 50, 555), and in autoimmune pathologies and graft-versus host pathology (Piguet, P. -F. et al., *J. Exp. Med.* 1987, 166, 1280). The association of TNFα with cancer and infectious pathologies is often related to the host's catabolic state. A major problem in cancer patients is weight loss, usually associated with anorexia. The extensive wasting which results is known as "cachexia" (Kern, K. A. al., *J. Parent. Enter. Nutr.* 1988, 12, 286–298). Cachexia includes progressive weight loss, anorexia, and persistent erosion of body mass in response to a malignant growth. The fundamental physiological derangement may be related to a decline in food intake relative to energy expenditure. The cachectic state is thus associated with significant morbidity and is responsible for the majority of cancer mortality. A number of studies have suggested that TNFα is an important mediator of the cachexia in cancer, infectious pathology, and in other catabolic states.

TNFα is thought to play a central role in the pathophysiological consequences of Gram-negative sepsis and endotoxic shock (Michie, H. R. et al., *Br. J. Surg.* 1989, 76, 670–671; Debets, J. M. H. et al., *Second Vienna Shock Forum,* 1989, p.463–466; Simpson, S. Q. et al., *Crit. Care Clin.* 1989, 5, 27–47), including fever, malaise, anorexia, and cachexia. Endotoxin is a potent monocyte/macrophage activator which stimulates production and secretion of TNFα (Kornbluth, S. K. et al., *J. Immunol.* 1986, 137, 2585–2591) and other cytokines. Because TNFα could mimic many biological effects of endotoxin, it was concluded to be a central mediator responsible for the clinical manifestations of endotoxin-related illness. TNFα and other monocyte-derived cytokines mediate the metabolic and neurohormonal responses to endotoxin (Michie, H. R. et al., *N. Eng. J. Med.* 1988, 318, 1481–1486). Endotoxin administration to human volunteers produces acute illness with flu-like symptoms including fever, tachycardia, increased metabolic rate and stress hormone release (Revhaug, A. et al., *Arch. Surg.* 1988, 123, 162–170). Elevated levels of circulating TNFα have also been found in patients suffering from Gram-negative sepsis (Waage, A. et al., *Lancet* 1987, 1, 355–357). Treatment of cancer patients with TNFα (because of its tumoricidal action) revealed that doses greater than 545 $\mu g/m^2/24$ hours caused alterations similar to those induced by injection of endotoxin (4 ng/kg) into healthy humans (Michie, H. R. et al., *Surgery* 1988, 104, 280–286), supporting TNFα's role as the principal host mediator of septic and endotoxemic responses. Chronic intravenous TNFα infusion into humans or rats was associated with anorexia, fluid retention, acute phase responses, and negative nitrogen balance (i.e., classic catabolic effects), leading to the conclusion that TNFα may be responsible for many of the changes noted during critical illness (Michie, H. R. et al., *Ann. Surg.* 1989, 209, 19–24).

The numerous biological effects of TNFα and the closely related cytokine, TNFβ (lymphotoxin), are mediated by two transmembrane receptors, both of which have been cloned. The p55 receptor (also termed TNF-R55, TNF-RI, or TNFRβ) is a 55 kd glycoprotein shown to transduce signals resulting in cytotoxic, anti-viral, and proliferative activities of TNFα.

The p75 receptor (also termed TNF-R75, TNF-RII, or TNFRα) is a 75 kd glycoprotein that has also been shown to transduce cytotoxic and proliferative signals as well as signals resulting in the secretion of GM-CSF.

The extracellular domains of the two receptors are 28% identical in primary structure and have in common a set of four subdomains defined by numerous conserved cysteine residues. The p75 receptor differs, however, by having a region adjacent to the transmembrane domain that is rich in proline residues and contains sites for 0-linked glycosylation. Interestingly, the cytoplasmic domains of the two receptors share no apparent homology which is consistent with observations that they can transduce different signals to the interior of the cell.

TNFα inhibitors have been detected in normal human urine and in serum of patients with cancer or endotoxemia. These have since been shown to be the receptor extracellular domains derived by proteolytic cleavage of the transmembrane forms. Many of the same stimuli that result in TNFα release also result in the release of the soluble receptors, suggesting that these soluble TNFα inhibitors may serve as part of a negative feedback mechanism to control TNFα activity (Porteu, F. and C. Nathan (1990) *J. Exp. Med.* 172:599–607; and, Adreke, D. et al., (1992) *J. Exp. Med.* 175:323–329).

There is a need for compounds which effectively inhibit TNFα activity. There is a need to provide compounds that bind to TNFα with high affinity and can prevent TNFα from binding to its receptors. There is a need for compounds which can neutralize TNFα activity in vivo.

SUMMARY OF THE INVENTION

The present invention relates to TNFα antagonist compounds that comprise a molecular surface that is substantially similar to at least one molecular surface of human TNFα selected from the group of molecular surfaces of human TNFα consisting of: the molecular surface of human TNFα at amino acids 107–110; the molecular surface of human TNFα at amino acids 42–49; the molecular surface of human TNFα at amino acids 20–26; the molecular surface of human TNFα at amino acids 30–36; and the molecular surface of human TNFα at amino acids 86–89. The TNFα antagonist compounds bind to TNF p55 receptor and/or TNF p75 receptor and inhibit TNFα mediated cytotoxicity.

The present invention relates to peptides which inhibit TNFα activity and which have the formula:
a) $R_1-R_2-R_3-R_4-R_5-R_6-R_7$
wherein:
  $R_1$ is a linking moiety;
  $R_2$ is 0–10 amino acids;
  $R_3$ is Glu or Asp;
  $R_4$ is a spacing moiety;
  $R_5$ is Glu or Asp;
  $R_6$ is 0–10 amino acids;
  $R_7$ is a linking moiety;
and wherein $R_1$, $R_2$, $R_3$, $R_4$, $R_5$, $R_6$ and $R_7$, taken together, are less than 25 amino acids, said peptides are TNFα antagonists, have a restricted conformation, bind to TNF p55 receptor and/or TNF p75 receptor;
b) $R_{11}-R_{12}-R_{13}-R_{14}-R_{15}-R_1-R_{17}$
wherein:
  $R_{11}$ is a linking moiety;
  $R_{12}$ is 0–10 amino acids;
  $R_{13}$ is a spacing moiety;
  $R_{14}$ is Ser-Tyr-Gln, dSer-Tyr-Gln or Ser-dTyr-Gln;
  $R_{15}$ is a spacing moiety;
  $R_{16}$ is 0–10 amino acids;
  $R_{17}$ is a linking moiety;
and wherein $R_{11}$, $R_{12}$, $R_{13}$, $R_{14}$, $R_{15}$, $R_{16}$ and $R_{17}$, taken together are less than 25 amino acids, said peptides are TNFα antagonists, have a restricted conformation, bind to TNF p55 receptor and/or TNF p75 receptor;
c) Cys-Ala-Arg-Asp-Asn-Gln-Ala-Cys SEQ ID NO:1;
d) Cys-Pro-Gln-Ala-Glu-Gly-Gln-Leu-Cys SEQ ID NO:2; or
e) Cys-Arg-Arg-Ala-Asn-Ala-dCys.

The present invention relates to a method of inhibiting tumor necrosis factor-alpha activity. The method comprises the step of contacting cells that have tumor necrosis factor receptors with a TNFα antagonist compound. The TNF antagonsait compound comprises a molecular surface that is substantially similar to at least one molecular surface of human TNFα selected from the group of molecular surfaces of human TNFα consisting of: the molecular surface of human TNFα at amino acids 107–110; the molecular surface of human TNFα at amino acids 42–49; the molecular surface of human TNFα at amino acids 20–26; the molecular surface of human TNFα at amino acids 30–36; and the molecular surface of human TNFα at amino acids 86– 89. The TNFα antagonist compound binds to TNF p55 receptor and/or TNF p75 receptor and inhibits TNFα mediated cytotoxicity.

The present invention relates to a method of inhibiting tumor necrosis factor-alpha activity comprising the step of contacting cells that tumor necrosis factor receptors with a peptide that inhibits TNFα activity and has the formula:
a) $R_1-R_2-R_3-R_4-R_5-R_5-R_7$
wherein:
  $R_1$ is a linking moiety;
  $R_2$ is 0–10 amino acids;
  $R_3$ is Glu or Asp;
  $R_4$ is a spacing moiety;
  $R_5$ is Glu or Asp;
  $R_6$ is 0–10 amino acids;
  $R_7$ is a linking moiety;
and wherein $R_1$, $R_2$, $R_3$, $R_4$, $R_5$, $R_6$ and $R_7$, taken together, are less than 25 amino acids, said peptides are TNFα antagonists, have a restricted conformation, bind to TNF p55 receptor and/or TNF p75 receptor;
b) $R_{11}-R_{12}-R_{13}-R_{14}-R_{15}-R_{16}-R_{17}$
wherein:
  $R_{11}$ is a linking moiety;
  $R_{12}$ is 0–10 amino acids;
  $R_{13}$ is a spacing moiety;
  $R_{14}$ is Ser-Tyr-Gln, dSer-Tyr-Gln or Ser-dTyr-Gln;
  $R_{15}$ is a spacing moiety;
  $R_{16}$ is 0–10 amino acids;
  $R_{17}$ is a linking moiety;
and wherein $R_{11}$, $R_{12}$, $R_{13}$, $R_{14}$, $R_{15}$, $R_{16}$ and $R_{17}$, taken together are less than 25 amino acids, said peptides are TNFα antagonists, have a restricted conformation, bind to TNF p55 receptor and/or NF p75 receptor;
c) Cys-Ala-Arg-Asp-Asn-Gln-Ala-Cys SEQ ID NO:1;
d) Cys-Pro-Gln-Ala-Glu-Gly-Gln-Leu-Cys SEQ ID NO:2; or
e) Cys-Arg-Arg-Ala-Asn-Ala-dCys.

The present invention relates to a method of treating an individual suspected of suffering from a disease or disorder mediated by tumor necrosis factor-alpha activity. The method comprises the step of administering to the individual a therapeutically effective amount of a TNFα antagonist compound. The TNFα antagonist compound comprises a molecular surface that is substantially similar to at least one molecular surface of human TNFα selected from the group of molecular surfaces of human TNFα consisting of: the molecular surface of human TNFα at amino acids 107–110; the molecular surface of human TNFα at amino acids 42–49; the molecular surface of human TNFα at amino acids 20–26; the molecular surface of human TNFα at amino acids 30–36; and the molecular surface of human TNFα at amino acids 86–89. The TNFα antagonist compound binds to TNF p55 receptor and/or TNF p75 receptor and inhibits TNFα mediated cytotoxicity.

The present invention relates to a method of treating an individual suspected of suffering from a disease or disorder mediated by tumor necrosis factor-alpha activity. The method comprises the step of administering to the individual a therapeutically effective amount of a peptide that inhibits tumor necrosis factor-alpha. The peptide has the formula:
a) $R_1-R_2-R_3-R_4-R_5-R_6-R_7$
wherein:
$R_1$ is a linking moiety;
$R_2$ is 0–10 amino acids;
$R_3$ is Glu or Asp;
$R_4$ is a spacing moiety;
$R_5$ is Glu or Asp;
$R_6$ is 0–10 amino acids;
$R_7$ is a linking moiety;
and wherein $R_1$, $R_2$, $R_3$, $R_4$, $R_5$, $R_6$ and $R_7$, taken together, are less than 25 amino acids, said peptides are TNFα antagonists, have a restricted conformation, bind to TNF p55 receptor and/or TNF p75 receptor;
b) $R_{11}-R_{12}-R_{13}-R_{14}-R_{15}-R_{16}-R_{17}$
wherein:
$R_{11}$ is a linking moiety;
$R_{12}$ is 0–10 amino acids;
$R_{13}$ is a spacing moiety;
$R_{14}$ is Ser-Tyr-Gln, dSer-Tyr-Gln or Ser-dTyr-Gln;
$R_{15}$ is a spacing moiety;
$R_{16}$ is 0–10 amino acids;
$R_{17}$ is a linking moiety;
and wherein $R_{11}$, $R_{12}$, $R_{13}$, $R_{14}$, $R_{15}$, $R_{16}$ and $R_{17}$, taken together are less than 25 amino acids, said peptides are TNFα antagonists, have a restricted conformation, bind to TNF p55 receptor and/or TNF p75 receptor;
c) Cys-Ala-Arg-Asp-Asn-Gln-Ala-Cys SEQ ID NO:1;
d) Cys-Pro-Gln-Ala-Glu-Gly-Gln-Leu-Cys SEQ ID NO:2; or
e) Cys-Arg-Arg-Ala-Asn-Ala-dCys.

DETAILED DESCRIPTION OF THE INVENTION

The present invention provides molecules that are TNFαinhibitors. The molecules of the present invention act as TNF receptor antagonists. The native TNFα molecules must compete with the molecules of the invention to bind to the TNF receptors. As TNFα antagonists, such molecules interact with TNF receptors but do not produce the same biological effect that is produced when TNFα interacts with the receptors. Thus, the molecules of the invention inhibit TNFα activity by competing with TNFα for binding to the TNF receptors.

As used herein, the term "compound" refers to molecules which include peptides and non-peptides including, but not limited to molecules which comprise amino acid residues joined by at least some non-peptidyl bonds. As used herein, the term "peptide" refers to polymers formed by naturally occurring amino acid subunits joined by peptide bonds. The term is meant to refer to naturally occurring subunits or their close homologs. The term amino acid may also refer to moieties which have portions similar to naturally occurring peptides but which have non-naturally occurring portions. Thus, peptides may have altered amino acids or linkages. Peptides may also comprise other modifications consistent with the spirit of this invention. Such peptides are best described as being functionally interchangeable yet structurally distinct from natural peptides. As used herein, the terms "compounds" and "peptides" are used interchangeably.

As used herein, "Pen" is meant to refer to penicillamine, 3-mercapto-D-valine, which is a by product of penicillin degradation and which contains a sulphur atom capable of forming a disulfide bond with the sulphur atom from another penicillamine molecule or a cysteine. The chemistry of penicillamine and its synthesis are reported in *The Merck Index, Tenth Edition* 1983 Merck and Company, Inc. Rahway N.J. on page 1017, which is incorporated herein by reference as are the citations listed therein.

As used herein, the term "linking moiety" is meant to refer to amino acids, particularly cysteine and penicillamine, and any other a molecular entity capable of forming bonds to two molecules at two separate sites.

As used herein, the term "spacer moiety" is meant to refer to a molecular entity which is capable of binding to two active functioning molecules at two separate sites and maintain the active functioning molecules in the proper orientation relative to each other such that the active functioning molecular entities interact with the TNF receptors.

As used herein, the terms "active functioning molecule" and "active functioning molecular entity" are used interchangeably and are meant to refer to moieties which present the proper functional groups to form a surface which interacts with the TNF receptors.

According to the present invention, compounds are provided which bind to TNF receptors in competition with TNFα. When bound to the TNF receptors, the compounds do not have the same biological effect as that which occurs when TNFα binds to the receptor. Rather, the compounds are antagonists which essentially prevent TNFα from binding to p55 and p75 receptors. Accordingly, the compounds are TNFα inhibitors. By inhibiting such TNFα/TNF receptor binding, the compounds of the invention inhibit the biological activity of TNFα. By blocking TNFα from binding to its receptors, the compounds of the invention prevent TNFα from producing the biological effect associated with the TNFα-TNF receptor binding.

The compounds of the present invention are TNFα antagonists. The compounds comprise a molecular surface that is substantially similar to at least one molecular surface of human TNFα selected from the group of molecular surfaces of human TNFα consisting of: the molecular surface of human TNFα at amino acids 107–110; the molecular surface of human TNFα at amino acids 42–49; the molecular surface of human TNFα at amino acids 20–26; the molecular surface of human TNFα at amino acids 30–36; and the molecular surface of human TNFα at amino acids 86–89. However, while the compounds bind to TNF receptors by mimicking a surface of human TNF, the compounds do not produce the same biological effect as that which occurs when TNFα binds to a TNF receptor. An example of a biological effect which can be detected by assay is TNF cytotoxicity. Thus, the TNF antagonist compounds compete with native TNFα for binding to TNF receptor but do not produce the same biological effect when bound to a TNF receptor as that which is produced when TNFαbinds to a TNF receptor. Accordingly, the TNF antagonist compounds of the invention are effective inhibitors of TNFα by competing with TNFα for binding to TNF receptors and thereby preventing TNFα from binding to TNF receptors.

In some embodiments of the present invention, the compounds have the formula:

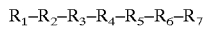

$R_1-R_2-R_3-R_4-R_5-R_6-R_7$ wherein:
- $R_1$ is a linking moiety;
- $R_2$ is 0–10 amino acids;
- $R_3$ is Glu or Asp;
- $R_4$ is a spacing moiety;
- $R_5$ is Glu or Asp;
- $R_6$ is 0–10 amino acids;
- $R_7$ is a linking moiety;
- wherein $R_1$, $R_2$, $R_3$, $R_4$, $R_5$, $R_6$ and $R_7$, taken together, are less than 25 amino acids. The peptides of the invention have a restricted conformation, bind to TNF p55 receptor and/or TNF p75 receptor as a TNFα antagonist.

The purpose of $R_1$ and $R_7$ is to cyclicize the molecule and thereby maintain $R_2$–$R_3$–$R_4$–$R_5$–$R_6$ in a constrained conformation which produces a specific biologically active surface. Accordingly, $R_1$ and $R_7$ may be any moieties capable of forming bonds with each other and $R_2$ and $R_6$, respectively. $R_1$ and $R_7$ may each be amino acids which can cyclicize the peptides by peptide bonds. In some preferred embodiments, $R_1$ and $R_7$ may independently be cysteine or penicillamine. When both $R_1$ and $R_7$ are cysteine or penicillamine, the molecule may be cyclicized by the formation of disulfide bonds between $R_1$ and $R_7$ and the formation of peptides bonds between $R_1$ and $R_2$ and between $R_7$ and $R_6$. In addition to cyclization by the formation of disulfide bonds between two terminal cysteines such as when $R_1$ and $R_7$ are both cysteine, $R_1$ and $R_7$ may each be any other moiety that will allow for the cyclization of the molecule. That is, $R_1$ may be any moiety capable of forming bonds with both $R_2$ and $R_7$ and $R_7$ may be any moiety capable of forming bonds with both $R_1$ and $R_6$. When $R_1$ is cysteine, it is preferred that $R_7$ is also cysteine. Those having ordinary skill in the art can readily prepare peptides according to the present invention in which $R_1$ and $R_7$ are moieties capable of forming bonds to each other. In preferred embodiments, $R_1$ and $R_7$ are both cysteine and are linked to each other by an intermolecular disulfide bond.

$R_2$ does not directly participate in the active surface of the molecule and, in some embodiments, is not necessary for the molecule to be an active inhibitor of TNFα activity. In preferred embodiments, $R_2$ is 0–5 amino acids. In some embodiments, $R_2$ is 5 amino acids. In some embodiments, $R_2$ is 4 amino acids. In some embodiments, $R_2$ is 3 amino acids. In some embodiments, $R_2$ is 2 amino acids. In some embodiments, $R_2$ is 1 amino acid. In some embodiments, $R_2$ is 0 amino acids. In some embodiments, $R_2$ may be Pro-Arg-Glu-Thr-Pro SEQ ID NO:3, Pro-Glu-Thr-Pro SEQ ID NO:4 or Thr-Pro.

$R_3$ is directly involved in the active portion of the molecules of the invention. $R_3$ may be glutamic acid or aspartic acid. It is also contemplated that a moiety which contributes the same or similar surface may be used in place of glutamic acid or aspartic acid. Examples of such moieties are molecules which have the same or similar functional groups as glutamic acid or aspartic acid but which have variations in the backbone.

$R_4$ is a spacer moiety which has been found to be critical in its function of maintaining and supporting $R_3$ and $R_5$ in proper positions relative to each other. Examples of $R_4$ spacer moieties capable of proper spacing of $R_3$ and $R_5$ include amino isobutyric acid (AIB), Gly-Ala, Gly-Gly, Ala-Gly, and Ala-Ala. Other contemplated spacers include Gly-Leu, Gly-Ile, Gly-Val, Ala-Leu, Ala-Ile, Ala-Val, Leu-Ala, Leu-Gly, Leu-Leu, Leu-Ile, Leu-Val, Ile-Ala, Ile-Gly, Ile-Leu, Ile-Ile, Ile-Val, Val-Ala, Val-Gly, Val-Leu, Val-Ile and Val-Val. In addition, other molecular entities which can maintain and support $R_3$ and $R_5$ in proper positions relative to each other can be used as spacer moieties of $R_4$.

$R_5$ is directly involved in the active portion of the molecules of the invention. $R_5$ may be glutamic acid or aspartic acid. It is also contemplated that a moiety which contributes the same or similar surface may be used in place of glutamic acid or aspartic acid. Examples of such moieties are molecules which have the same or similar functional groups as glutamic acid or aspartic acid but which have variations in the backbone.

$R_6$ does not directly participate in the active surface of the molecule and, in some embodiments, is not necessary for the molecule to be an active inhibitor of TNFα activity. In preferred embodiments, $R_6$ is 0–5 amino acids. In some embodiments, $R_6$ is 5 amino acids. In some embodiments, $R_6$ is 4 amino acids. In some embodiments, $R_6$ is 3 amino acids. In some embodiments, $R_6$ is 2 amino acids. In some embodiments, $R_6$ is 1 amino acid. In some embodiments, $R_6$ is 0 amino acids. In some embodiments, $R_6$ may be Ala-Lys-Pro, or Ala.

In some embodiments, the molecules of the invention present a surface contributed by $R_3$–$R_4$–$R_5$ in which the components are conformationally restricted as a cyclicized entity. In some embodiments, $R_3$–$R_4$–$R_5$ is Glu-AIB-Glu. In some embodiments, $R_3$–$R_4$–$R_5$ is Glu-Gly-Ala-Glu SEQ ID NO:5.

In some preferred embodiments, $R_2$ is 0 amino acids, $R_6$ is 0 amino acids and $R_1$ and $R_7$ are cysteine or penicillamine. Accordingly, molecules of the invention may include Cys-Glu-AIB-Glu-Cys SEQ ID NO:6, Pen-Glu-AIB-Glu-Pen SEQ ID NO:7, Cys-Glu-Gly-Ala-Glu-Cys SEQ ID NO:8 and Pen-Glu-Gly-Ala-Glu-Pen SEQ ID NO:9.

In some embodiments, $R_1$ and $R_7$ are cysteine or penicillamine, $R_2$ is 0–5 amino acids and $R_6$ is 0–5 amino acids. In some embodiments the molecule is Cys-Pro-Arg-Glu-Thr-Pro-Glu-Gly-Ala-Glu-Ala-Lys-Pro-Cys SEQ ID NO:10, Cys-Pro-Glu-Thr-Pro-Glu-Gly-Ala-Glu-Ala-Lys-Pro-Cys SEQ ID NO:11, Pen-Thr-Pro-Glu-Gly-Ala-Glu-Ala-Pen SEQ ID NO:12.

In some embodiments, the compounds of the invention have the formula:

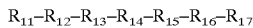

$R_{11}-R_{12}-R_{13}-R_{14}-R_{15}-R_{16}-R_{17}$ wherein:
- $R_{11}$ is a linking moiety;
- $R_{12}$ is 0–10 amino acids;
- $R_{13}$ is a spacing moiety;
- $R_{14}$ is Ser-Tyr-Gln, dSer-Tyr-Gln or Ser-dTyr-Gln;
- $R_{15}$ is a spacing moiety;
- $R_{16}$ is 0–10 amino acids;
- $R_{17}$ is a linking moiety;
and wherein $R_{11}$, $R_{12}$, $R_{13}$, $R_{14}$, $R_{15}$, $R_{16}$ and $R_{17}$, taken together are ss than 25 amino acids. The peptides of the invention have restricted conformation and inhibit TNFα activity.

The purpose of $R_{11}$ and $R_{17}$ is to cyclicize the molecule d thereby maintain $R_{12}$–$R_{13}$–$R_{14}$–$R_{15}$–$R_{16}$ in a constrained information which produces a specific biologically active surface. Accordingly, $R_{11}$ and $R_{17}$ may be any moieties capable of forming bonds with each other and $R_{12}$ and $R_{16}$, respectively. $R_1$ and $R_7$ may each be amino acids which can cyclicize the peptides by peptide bonds. In some preferred embodiments, $R_{11}$ and $R_{17}$ may independently be cysteine or penicillamine. When both $R_{11}$ and $R_{17}$ are cysteine or penicillamine, the molecule may be cyclicized by the formation of disulfide bonds between $R_{11}$ and $R_{17}$ and the formation of peptides bonds between $R_{11}$ and $R_{12}$ and between $R_{17}$ and $R_{16}$. In addition to cyclization by the formation of disulfide bonds between two terminal cysteines such as when $R_{11}$ and $R_{17}$ are both cysteine, $R_{11}$ and $R_{17}$ may each be any other moiety that will allow for the cyclization of the molecuile. That is, $R_{11}$ may be any moiety capable of forming bonds with both $R_{12}$ and $R_{17}$ and $R_{17}$ may be any moiety capable of forming bonds with both $R_{11}$ and $R_{16}$. When $R_{11}$ is cysteine, it is preferred that $R_{17}$ is also cysteine. Those having ordinary skill in the art can readily prepare peptides according to the present invention in which $R_{11}$ and $R_{17}$ are moieties capable of forming bonds to each other. In preferred embodiments, $R_{11}$ and $R_{17}$ are both cysteine and are linked to each other by an intermolecular disulfide bond.

$R_{12}$ does not directly participate in the active surface of the molecule, and in some embodiments, is not necessary for the molecule to be an active inhibitor of TNFα activity. $R_{12}$ can be provided to maintain $R_{14}$ in proper conformation. In preferred embodiments, $R_{12}$ is 0–5 amino acids. In some embodiments, $R_{12}$ is 5 amino acids. In some embodiments, $R_{12}$ is 4 amino acids. In some embodiments, $R_{12}$ is 3 amino acids. In some embodiments, $R_{12}$ is 2 amino acids. In some embodiments, $R_{12}$ is 1 amino acid. In some embodiments, $R_{12}$ is 0 amino acids. Examples of $R_{12}$ include, but are not limited to, Arg-Ile-Ala-Val SEQ ID NO:13, Ile-Ala-Val, Ile-Ala and Ala. It is contemplated that these examples of $R_{12}$ can contain conservative substitutions such as, the Ile in Arg-Ile-Ala-Val SEQ ID NO:13, Ile-Ala-Val and Ile-Ala can be substituted with Gly, Val, Ala or Leu. Similarly, the Ala in Arg-Ile-Ala-Val SEQ ID NO:13, Ile-Ala-Val, Ile-Ala and Ala can be substituted with Gly, Val, Ile or Leu. Likewise, the Val in Arg-Ile-Ala-Val SEQ ID NO:13 and Ile-Ala-Val can be substituted with Gly, Ile, Ala or Leu.

$R_{13}$ is a spacer moiety which can be provided to maintain $R_{14}$ in proper conformation. $R_{13}$ is optional, wherein when $R_{13}$ is not present, it can be expressed as $R_{13}$ is 0 amino acids. Examples of $R_{13}$ spacer moieties include 0 amino acids, amino isobutyric acid (AIB), Gly-Ala, Gly-Gly, Ala-Gly, and Ala-Ala. Other contemplated spacers include Gly-Leu, Gly-Ile, Gly-Val, Ala-Leu, Ala-Ile, Ala-Val, Leu-Ala, Leu-Gly, Leu-Leu, Leu-Ile, Leu-Val, Ile-Ala, Ile-Gly, Ile-Leu, Ile-Ile, Ile-Val, Val-Ala, Val-Gly, Val-Leu, Val-Ile and Val-Val. In addition, other molecular entities which can maintain $R_{14}$ in proper conformation can be used as spacer moieties at $R_{13}$.

$R_{14}$ is selected from the group consisting of Ser-Tyr-Gln, dSer-Tyr-Gln and Ser-dTyr-Gln. Alternatively, it is contemplated that $R_{14}$ can contain conservative substitutions, such as, for example, Ser can be replaced by Thr, Tyr can be replaced by Phe, and/or Gln can be replaced by Asn. It is also contemplated $R_{14}$ can be a moiety that contributes the same or similar surface as that which is formed by Ser-Tyr-Gln, dSer-Tyr-Gln or Ser-dTyr-Gln. Examples of such moieties are molecules which have the same or similar functional groups as Ser-Tyr-Gln, dSer-Tyr-Gln and Ser-dTyr-Gln but which have variations in the backbone.

$R_{15}$ is a spacer moiety which can be provided to maintain $R_{14}$ in proper conformation. $R_{15}$ is optional, wherein when $R_{15}$ is not present, it can be expressed as $R_{15}$ is 0 amino acids. Examples of $R_{15}$ spacer moieties include 0 amino acids, amino isobutyric acid (AIB), Gly-Ala, Gly-Gly, Ala-Gly, and Ala-Ala. Other contemplated spacers include Gly-Leu, Gly-Ile, Gly-Val, Ala-Leu, Ala-Ile, Ala-Val, Leu-Ala, Leu-Gly, Leu-Leu, Leu-Ile, Leu-Val, Ile-Ala, Ile-Gly, Ile-Leu, Ile-Ile, Ile-Val, Val-Ala, Val-Gly, Val-Leu, Val-Ile and Val-Val. In addition, other molecular entities which can maintain $R_{14}$ in proper conformation can be used as spacer moieties at $R_{15}$.

$R_{16}$ does not directly participate in the active surface of the molecule and, in some embodiments, is not necessary for the molecule to be an active inhibitor of TNFα activity. $R_{16}$ can be provided to maintain $R_{14}$ in proper conformation. In preferred embodiments, $R_{16}$ is 0–5 amino acids. In some embodiments, $R_{16}$ is 5 amino acids. In some embodiments, $R_{16}$ is 4 amino acids. In some embodiments, $R_{16}$ is 3 amino acids. In some embodiments, $R_{12}$ is 2 amino acids. In some embodiments, $R_{16}$ is 1 amino acids. In some embodiments, $R_{16}$ is 0 amino acids. Examples of $R_{16}$ include, but are not limited to, Thr-Lys-Val and Thr-Lys. It is contemplated that these examples of $R_{16}$ can contain conservative substitutions such as, the Thr in Thr-Lys-Val and Thr-Lys can be substituted with Ser. Similarly, the Lys in Thr-Lys-Val and Thr-Lys can be substituted with hydroxylysine, Val, Ala or Leu. Likewise, the Val in Thr-Lys-Val can be substituted with Gly, Ile, Ala or Leu.

The molecules of the invention present a surface contributed by $R_{14}$ in which the components are conformationally restricted as a cyclicized entity. $R_{11}$ and $R_{17}$ function to conformationally restrict $R_{14}$, $R_{12}$, $R_{13}$, $R_{15}$ and $R_{16}$ function to maintain $R_{14}$ in the proper conformation.

In some preferred embodiments, the compounds of the invention is: Cys-Ser-Tyr-Gln-Thr-Lys-Val-Cys SEQ ID NO:14; Cys-Arg-Ile-Ala-Val-Ser-Tyr-Gln-Thr-Lys-Val-Cys SEQ ID NO:15; Cys-Ser-Tyr-Gln-Thr-Lys-Cys SEQ ID NO:16; Cys-Ile-Ala-Val-Ser-Tyr-Gln-Thr-Lys-Cys SEQ ID NO:17; Cys-Ile-Ala-AIB-Ser-Tyr-Gln-Thr-Lys-Cys SEQ ID NO:18; Cys-Ala-AIB-dSer-Tyr-Gln-Cys; or Cys-Ala-AIB-Ser-dTyr-Gln-Cys.

In some embodiments of the invention, the compound is Cys-Ala-Arg-Asp-Asn-Gln-Ala-Cys SEQ ID NO:1. It is contemplated that one or more of the amino acids in this compound may be deleted or substituted with a conservative substitution such as, for example: one or both of the Cys residues may be substituted, independently, with Penicillamine, dCys or dPenicillamine; one or both of the Ala residues may be substituted, independently, with Gly, Val, Leu or Ile; Asp may be substituted with Glu; Asn may be substituted with Gln; and/or Gln may be substituted with Asn.

In some embodiments of the invention, the compound is Cys-Pro-Gln-Ala-Glu-Gly-Gln-Leu-Cys SEQ ID NO:2. It is contemplated that one or more of the amino acids in this compound may be deleted or substituted with a conservative substitution such as, for example: one or both of the Cys residues may be substituted, independently, with Penicillamine, dCys or dPenicillamine; Pro may be substituted with hydroxyproline; one or both of the Gln residues may be substituted, independently, with Asn; Ala residues may be substituted with Gly, Val, Leu or Ile; Glu may be substituted with Asp; Gly may be substituted with Ala, Val, Leu or Ile; and/or Leu may be substituted with Ala, Val, Gly or Ile.

In some embodiments of the invention, the compound is Cys-Arg-Arg-Ala-Asn-Ala-dCys. It is contemplated that one or more of the amino acids in this compound may be deleted or substituted with a conservative substitution such as, for example: Cys may be substituted with Penicillamine, dCys or dPenicillamine; one or both of the Ala residues may be substituted, independently, with Gly, Val, Leu or Ile; Asn may be substituted with Gln; and/or dCys may be substituted with dPenicillamine, Cys or Penicillamine.

In some embodiments, peptides of the present invention comprise one or more D amino acids. As used herein, the term "D amino acid peptides" is meant to refer to peptides according to the present invention which comprise at least one and preferably a plurality of D amino acids. D amino acid peptides retain the biological activity of the peptides of the invention that consist of L amino acids, i.e. D amino acid peptides inhibit TNFα. In some embodiments, the use of D amino acid peptides is desirable as they are less vulnerable to degradation and therefore have a longer half life. In some embodiments, D amino acid peptides comprise mostly all D amino acids. In some embodiments, D amino acid peptides that consist of only D amino acids may comprise amino acid sequences in the reverse order of amino acid sequences of peptides whose sequences are set out herein.

As used herein, the term "derivatives" refers to peptides of the invention which have the amino terminal and/or the carboxy terminal blocked, particularly those in which the amino group of the N terminal residue is acetylated and/or the carboxy group of the C terminal residue is amidated.

In addition to derivatives and conservative analogs, the present invention contemplates compounds which display substantially the same surface as the peptides of the invention. As used herein, the term "mimetics" is meant to refer to compounds that are not peptides but that comprise a similar surface as the peptides of the invention and can thus interact with the TNF receptor in a similar fashion as the peptides of the invention. Mimetics inhibit TNFα by interacting with TNF receptors in the same manner as the peptides of the invention. Mimetics have a molecular surface similar to one of a peptide of the invention. By providing a similar surface involved in intermolecular interactions, mimetics perform essentially the same function by essentially the same means to achieve essentially the same result as the peptides of the invention.

Peptides of the invention, including D amino acid peptides, may be prepared using the solid-phase synthetic technique initially described by Merrifield, in *J. Am. Chem. Soc.*, 15:2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Block synthesis techniques may also be applied to both the solid phase and solution methods of peptide synthesis. Rather than sequential addition of single amino acid residues, preformed blocks comprising two or more amino acid residues in sequence are used as either starting subunits or subsequently added units rather than single amino acid residues.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In order to determine whether a peptide inhibits TNFα, one or more of several well known assays may be performed routinely by those of ordinary skill in the art using readily available starting materials. The ability a test compound to inhibit TNFα from binding to an isolated TNF receptor is measured in one such assay. Other assays include those which the ability of a TNFα inhibitor candidate, i.e. a test compound, to inhibit TNFα activity when TNFα is contacted with cells that react to the presence of TNFα. For example, TNFα is cytotoxic to some cells, such as WEHI cells, and assays can be used to measure the ability a test compound, to inhibit TNFαcytotoxicity.

There are numerous other assays which can be used to determine a test compound's ability to inhibit TNFα. In some assays, specific non-lethal effects of TNFα on some cells is used as an end point to evaluate the TNFα inhibitory activity of a test compound. Known effects of TNFα on fibroblast cells include effects on mitogenesis, IL-6 secretion and HLA class II antigen induction. Comparisons can be made between TNFα's effect on fibroblasts in the presence or absence of a test compound using these detectable phenotypic changes as endpoints. Similarly, known effects of TNFα on monocyte cells include effects on secretion of cytokines such as GMCSF, IL-6 and IL-8. Comparisons can be made between TNFα's effect on cytokine secretion by monocytes in the presence or absence of a test compound. Additionally, TNFα is known to have effects on secretion of cytokine by endothelial cells and similar assays may be designed and performed. Further, TNFα is also known to effect adhesion molecule induction, ICAM-1, E-selectin, VCAM and tissue factor production in endothelial cells. Comparisons can be made between TNFα's effect on endothelial cells in the presence or absence of a test compound using these detectable phenotypic changes as endpoints as well.

Likewise, TNFα is known to effect neutrophils in specific ways. Comparisons can be made between TNFα's effect on neutrophils in the presence or absence of a test compound using activation, priming, degranulation and superoxide production as detectable endpoints for evaluation of TNFα inhibitory activity. These and other assays are well known to those having ordinary skill in the art. Such assays may be designed and performed routinely form readily available starting materials.

The TNFα inhibitors according to the invention are useful for treating a vertebrate having a pathology or condition associated with levels of a substance reactive with a TNF receptor, in particular TNFα, in excess of the levels present in a normal healthy subject. Such pathologies include, but are not limited to: sepsis syndrome, including cachexia; circulatory collapse and shock resulting from acute or chronic bacterial infection; acute and chronic parasitic or infectious processes, including bacterial, viral and fungal infections; acute and chronic immune and autoimmune pathologies, such as systemic lupus erythematosus and rheumatoid arthritis; alcohol-induced hepatitis; chronic inflammatory pathologies such as sarcoidosis and Crohn's pathology; vascular inflammatory pathologies such as disseminated intravascular coagulation; graft-versus-host pathology; Rawasaki's pathology; and malignant pathologies involving TNFα-secreting tumors.

Individuals who are suffering from or who are susceptible to such pathologies, conditions, diseases and disorders may be routinely identified by those having ordinary skill in the art using well known diagnostic and screening procedures.

Treatment of individuals comprises administering a single or multiple doses of a compound of the invention. Preferred for human pharmaceutical use are pharmaceutical compositions that comprise the compounds of the present invention in combination with a pharmaceutically acceptable carrier or diluent.

The pharmaceutical compositions of the present invention may be administered by any means that enables the active agent to reach the agent's site of action in the body of a mammal. In the case of the peptides of the invention, the primary focus is the ability to reach and bind with TNF receptors. Because proteins are subject to being digested when administered orally, parenteral administration, i.e., intravenous, subcutaneous, intramuscular, would ordinarily be used to optimize absorption. In some preferred embodiments, pharmaceutical compositions which comprise the compounds of the present invention are administered intravenously or subcutaneously.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

For parenteral administration, the TNFα inhibitor can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field.

For example, a parenteral composition suitable for administration by injection is prepared by dissolving 1.5% by weight of active ingredient in 0.9% sodium chloride solution.

EXAMPLES

In vitro cytotoxicity assay Cell line

The murine fibrosarcoma cell line L929 is widely used for testing TNF-α cytotoxicity in vitro. In addition, other cell lines are available that are more sensitive, such as the WEHI 164, a mouse myosarcoma cell line. Both cell lines were initially screened for use in the following experiments and WEHI 164 cells were chosen for their higher sensitivity.

Cells are maintained in serum free medium Ultraculture (Biowhittaker) with the addition of 2 mM Glutamine. The assay is carried out in the same serum free medium.

In the cytotoxicity assay, a susceptible cell line (WEHI 164) is incubated in medium containing serial dilutions of TNF-α for a set time and the consequent cytotoxic activity, manifested as inhibition of cell growth and/or cell death, is evaluated by spectrophotometer measurements of vital dye uptake.

Peptide solutions

Peptide stock solutions are made in HBSS at the concentration of 1 mg/ml, sterilized by passage through a 0.20 μm×13 mm cellulose acetate filters (Corning). The solutions were used for no longer than 10 days. All the other dilutions needed for the test were prepared just before the assay in sterile manner using the medium Ultraculture.

Procedure

WEHI 164 cells are taken from logarithmic growth and seeded in 96 well microtiter plates at the density of 2500 cells/well. The assay is performed 48 hours later, at a cell density of approximately 3000 cells/well. Cells are pre-incubated with serial dilutions of peptides for 30 minutes, then TNF-α is added to the wells and incubated for 16 hours at 37° C. Samples are repeated in triplicate.

Control wells for non treated cells contain medium only. A concentration curve of TNF-α is performed for every assay at concentrations ranging between 200 and 1 ng/ml. A control for full protection from TNF-α cytotoxicity is carried out by pre-incubating TNF-α with A2 antibody (Centocor, Malvern Pa.) for 30 minutes then adding it to the cells.

Detection

After 16 hour incubation, the vital dye AlamarBlue (Alamar Biosciences) is added in the amount equal to 10% final volume. The plates are returned to the incubator for 6–10 hours.

Absorbance is evaluated at 570 nm, subtracting the background absorbance measured at 595 nm in a BioRad microtiter plate reader.

Values are expressed as a percentage of cell survival, where the control samples (containing medium only) are referred to as 100%.

Results

Peptide: 505 SEQ ID NO:10

Cys-Pro-Arg-Glu-Thr-Pro-Glu-Gly-Ala-Glu-Ala-Lys-Pro-Cys

|  | control | 100 µg/ml peptide | 50 µg/ml peptide | 25 pg/ml peptide | Antibody |
|---|---|---|---|---|---|
| % cell survival | 100 ± 6 | 62.7 ± 4 | 56.5 ± 3 | 46 ± 13 | 100 ng/ml 83 ± 13 |
|  | 100 ± 0.5 | 32.5 ± 3 | 27.0 ± 8 | 16.5 ± 3 | 300 ng/ml 93.7 ± 3 |

Peptide: 506 SEQ ID NO:11

Cys-Pro-Glu-Thr-Pro-Glu-Gly-Ala-Glu-Ala-Lys-Pro-Cys

|  | control | 25 µg/ml peptide | 2.5 µg/ml peptide | 5 ng/ml TNF | Antibody |
|---|---|---|---|---|---|
| % cell survival | 100 | 88.1 | 68 | 75 | 500 ng/ml 99 |

Peptide: 561 SEQ ID NO:8

Cys-Glu-Gly-Ala-Glu-Cys

|  | control | 100 µg/ml peptide | 50 µg/ml peptide | 25 ng/ml TNF | Antibody |
|---|---|---|---|---|---|
| % cell survival | 100 ± 5 | 90 ± 10 | 92 ± 20 | 71 ± 9 | 500 ng/ml 87 ± 18 |

Peptide: 562 SEQ ID NO:12

Pen-Thr-Pro-Glu-Gly-Ala-Glu-Ala-Pen

|  | control | 100 µg/ml peptide | 50 µg/ml peptide | 25 pg/ml TNF | Antibody |
|---|---|---|---|---|---|
| % cell survival | 100 ± 0.5 | 33.1 ± 7 | 25.2 ± 7 | 16.5 ± 3 | 300 ng/ml 93.7 ± 3 |

Peptide: 556 SEQ ID NO:7

Pen-Glu-AIB-Glu-Pen

|  | control | 50 µg/ml peptide | 25 µg/ml peptide | 25 ng/ml TNF | Antibody |
|---|---|---|---|---|---|
| % cell survival | 100 ± 12 | 71 ± 14 | 69 ± 18 | 58 ± 7 | 500 ng/ml 99 ± 10 |

Peptide: 509 SEQ ID NO:1

Cys-Ala-Arg-Asp-Asn-Gln-Ala-Cys

|  | control | 25 µg/ml peptide | 2.5 µg/ml peptide | 25 ng/ml TNF | Antibody |
|---|---|---|---|---|---|
| % cell survival | 100 ± 0.1 | 28.4 | 21 ± 5 | 21 ± 3 | 500 ng/ml 95 ± 11 |

Peptide: 510 SEQ ID NO:2

Cys-Pro-Gln-Ala-Glu-Gly-Gln-Leu-Cs

|  | control | 100 µg/ml peptide | 50 µg/ml peptide | 25 pg/ml TNF | Antibody |
|---|---|---|---|---|---|
| % cell survival | 100 ± 6 | 60.4 ± 3 | 59.3 ± 1 | 46 ± 13 | 100 ng/ml 83 ± 13 |

Peptide: 512

Cys-Arg-Arg-Ala-Asn-Ala-dCys

|  | control | 100 µg/ml peptide | 50 µg/ml peptide | 25 pg/ml TNF | Antibody |
|---|---|---|---|---|---|
| % cell survival | 100 ± 6 | 65.6 ± 8 | 70.8 ± 6 | 46 ± 13 | 100 ng/ml 83 ± 13 |

Peptide: 521 SEQ ID NO:14

Cys-Ser-Tyr-Gln-Thr-Lys-Val-Cys

|  | control | 100 µg/ml peptide | 50 µg/ml peptide | 25 pg/ml TNF | Antibody |
|---|---|---|---|---|---|
| % cell survival | 100 ± 6 | 65.26 ± 4 | 56.51 ± 3 | 46 ± 13 | 100 ng/ml 83 ± 13 |

Peptide: 557 SEQ ID NO:15

Cys-Arg-Ile-Ala-Val-Ser-Tyr-Gln-Thr-Lys-Val-Cys

|  | control | 100 µg/ml peptide | 50 µg/ml peptide | 25 ng/ml TNF | Antibody |
|---|---|---|---|---|---|
| % cell survival | 100 ± 10 | 65 ± 4 | 70 ± 3 | 56 ± 3 | 500 ng/ml 80 ± 10 |

Peptide: 522 SEQ ID NO:16

Cys-Ser-Tyr-Gln-Thr-Lys-Cys

|  | control | 25 μg/ml peptide | 2.5 μg/ml peptide | 5 ng/ml TNF | Antibody |
|---|---|---|---|---|---|
| % cell survival | 100 | 111 | 81 | 85 | 500 ng/ml 102 |

Peptide: 558 SEQ ID NO:17

Cys-Ile-Ala-Val-Ser-Tyr-Gln-Thr-Lys-Cys

|  | control | 100 μg/ml peptide | 50 μg/ml peptide | 25 ng/ml TNF | Antibody |
|---|---|---|---|---|---|
| % cell survival | 100 ± 0.5 | 26 ± 7 | 24 ± 8 | 16 ± 4 | 300 ng/ml 94 ± 3 |

Peptide: 533 SEQ ID NO:18
Cys-Ile-Ala-AIB-Ser-Tyr-Gln-Thr-Lys-Cys

|  | control | 100 μg/ml peptide | 50 μg/ml peptide | 25 pg/ml TNF | Antibody |
|---|---|---|---|---|---|
| % cell survival | 100 ± 6 | 69.0 ± 5 | 46.8 ± 0.5 | 46 ± 13 | 100 ng/ml 83 ± 13 |

Peptide: 560
Cys-Ala-AIB-dSer-Tyr-Gln-Cys

|  | control | 100 μg/ml peptide | 50 μg/ml peptide | 25 ng/ml TNF | Antibody |
|---|---|---|---|---|---|
| % cell survival | 100 ± 3 | 68 ± 5 | 57 ± 17 | 56 ± 4 | 500 ng/ml 87 ± 10 |

Peptide: 621
Cys-Ala-AIB-Ser-dTyr-Gln-Cys

|  | control | 100 μg/ml peptide | 50 μg/ml peptide | 25 ng/ml TNF | Antibody |
|---|---|---|---|---|---|
| % cell survival | 100 ± 6 | 49.8 ± 4 | 53 ± 6 | 46 ± 13 | 100 ng/ml 84 ± 14 |

We claim:

1. A peptide that has the formula:

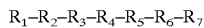

wherein:
- $R_1$ is cysteine or penicillamine;
- $R_2$ is 0–4 amino acids;
- $R_3$ is Glu or Asp;
- $R_4$ is selected from the group consisting of amino isobutyric acid (AIB), Gly-Ala, Gly-Gly, Ala-Gly, Ala-Ala, Gly-Leu, Gly-Ile, Gly-Val, Ala-Leu, Ala-Ile, Ala-Val, Leu-Ala, Leu-Gly, Leu-Leu, Leu-Ile, Leu-Val, Ile-Ala, Ile-Gly, Ile-Leu Ile-Ile, Ile-Val, Val-Ala, Val-Gly, Val-Leu, Val-Ile and Val-Val;
- $R_5$ is Glu or Asp;
- $R_6$ is 0–3 amino acids;
- $R_7$ is cysteine or penicillamine;

and wherein $R_1$, $R_2$, $R_3$, $R_4$, $R_5$, $R_6$ and $R_7$, taken together, are less than 15 amino acids, said peptides are TNFα antagonists, have a restricted conformation, and bind to TNF p55 receptor and/or TNF p75 receptor.

2. A peptide that has the formula:

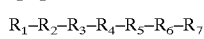

wherein:
- $R_1$ is cysteine or penicillamine;
- $R_2$ is Pro-Glu-Thr-Pro SEQ ID NO:4 or Thr-Pro;
- $R_3$ is Glu or Asp;
- $R_4$ is a spacing moiety;
- $R_5$ is Glu or Asp;
- $R_6$ is 0–3 amino acids;
- $R_7$ is cysteine or penicillamine;

and wherein $R_1$, $R_2$, $R_3$, $R_4$, $R_5$, $R_6$ and $R_7$, taken together, are less than 15 amino acids, said peptides are TNFα antagonists, have a restricted conformation, and bind to TNF p55 receptor and/or TNF p75 receptor.

3. A peptide that has the formula:

wherein:
- $R_1$ is cysteine or penicillamine;
- $R_2$ is 0 amino acids, Pro-Glu-Thr-Pro SEQ ID NO:4 or Thr-Pro;
- $R_3$ is Glu or Asp;
- $R_4$ is isobutyric acid (AIB), Gly-Ala, Gly-Gly, Ala-Gly, or Ala-Ala;

R$_5$ is Glu or Asp;

R$_6$ is 0 amino acids, Ala-Lys-Pro or Ala;

R$_7$ is cysteine or penicillamine;

and wherein R$_1$, R$_2$, R$_3$, R$_4$, R$_5$, R$_6$ and R$_7$, taken together, are less than 15 amino acids, said peptides are TNFα antagonists, have a restricted conformation, and bind to TNF p55 receptor and/or TNF p75 receptor.

4. A peptide that has the formula:

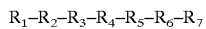

wherein:

R$_1$ is cysteine or penicillamine;

R$_2$ is 0, 1, 3, or 4 amino acids;

R$_3$ is Glu or Asp;

R$_4$ is selected from the group consisting of amino isobutyric acid (AIB), Gly-Ala, Gly-Gly, Ala-Gly, Ala-Ala, Gly-Leu, Gly-Ile, Gly-Val, Ala-Leu, Ala-Ile, Ala-Val, Leu-Ala, Leu-Gly, Leu-Leu, Leu-Ile, Leu-Val, Ile-Ala, Ile-Gly, Ile-Leu, Ile-Ile, Ile-Val, Val-Ala, Val-Gly, Val-Leu, Val-Ile and Val-Val;

R$_5$ is Glu or Asp;

R$_6$ is 0–2 amino acids;

R$_7$ is cysteine or penicillamine;

and wherein R$_1$, R$_2$, R$_3$, R$_4$, R$_5$, R$_6$ and R$_7$, taken together, are less than 15 amino acids, said peptides are TNFα, antagonists, have a restricted conformation, and bind to TNF p55 receptor and/or TNF p75 receptor.

5. A peptide that has the formula:

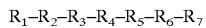

wherein:

R$_1$ is cysteine or penicillamine;

R$_2$ is 0 amino acids, Pro-Glu-Thr-Pro SEQ ID NO:4 or Thr-Pro;

R$_3$ is Glu or Asp;

R$_4$ is a isobutvric acid (AIB), Gly-Ala, Gly-Gly, Ala-Gly, or Ala-Ala;

R$_5$ is Glu or Asp;

R$_6$ is 0–3 amino acids;

R$_7$ is cysteine or penicillamine;

and wherein R$_1$, R$_2$, R$_3$, R$_4$, R$_5$, R$_6$ and R$_7$, taken together, are less than 15 amino acids, said peptides are TNFα antagonists, have a restricted conformation, and bind to TNF p55 receptor and/or TNF p75 receptor.

6. A compound that has the formula:

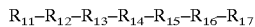

wherein:

R$_{11}$ is cysteine or penicillamine;

R$_{12}$ is 0–4 amino acids;

R$_{13}$ is a spacing moiety;

R$_{14}$ is dSer-Tyr-Gln or Ser-dTyr-Gln;

R$_{15}$ is a spacing moiety;

R$_{16}$ is 0–3 amino acids;

R$_{17}$ is cysteine or penicillamine;

and wherein R$_{11}$, R$_{12}$, R$_{13}$, R$_{14}$, R$_{15}$, R$_{16}$ and R$_{17}$, taken together are less than 15 amino acids, said peptides are TNFα antagonists, have a restricted conformation, and bind to TNF p55 receptor and/or TNF p75 receptor.

7. A compound that has the formula:

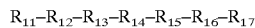

wherein:

R$_{11}$ and R$_{17}$ are independently, cysteine or penicillamine;

R$_{12}$ is 0–4 amino acids;

R$_{13}$ is a spacing moiety;

R$_{14}$ is dSer-Tyr-Gln- or Ser-dTyr-Gln;

R$_{15}$ is a spacing moiety;

R$_{16}$ is 0–3 amino acids;

and wherein R$_{11}$, R$_{12}$, R$_{13}$, R$_{14}$, R$_{15}$, R$_{16}$ and R$_{17}$, taken together are less than 15 amino acids, said peptides are TNFα antagonists, have a restricted conformation, and bind to TNF p55 receptor and/or TNF p75 receptor.

8. A peptide selected from the group consisting of:

a) a peptide having the sequence Cys-Ala-Arg-Asp-Asn-Gln-Ala-Cys SEQ ID NO:1;

b) a peptide having a sequence identical to SEQ ID NO:1 except for one or more conservative substitutions of amino acids in said SEQ ID NO:1;

c) a peptide having the sequence Cys-Arg-Arg-Ala-Asn-Ala-dCys; and d) a peptide having a sequence identical to Cys-Arg-Arg-Ala-Asn-Ala-dCys except for one or more conservative substitutions of amino acids in said sequence Cys-Arg-Arg-Ala-Asn-Ala-dCys.

9. The compound of claim 1 wherein R$_3$ is Glu.

10. The compound of claim 1 wherein R$_4$ is amino isobutyric acid (AIB), Gly-Ala, Gly-Gly, Ala-Gly, or Ala-Ala.

11. The compound of claim 1 wherein R$_5$ is Glu.

12. The compound of claim 6 wherein R$_{12}$ is 0 amino acids, Arg-Ile-Ala-Val SEQ ID NO:13, Ile-Ala-Val, Ile-Ala or Ala.

13. The compound of claim 6 wherein R$_{13}$ and R$_{15}$ are, independently, 0 amino acids or amino isobutyric acid.

14. The compound of claim 6 wherein R$_{16}$ is 0 amino acids, Thr-Lys-Val or Thr-Lys.

15. A TNFα antagonist having the formula

Cys-Ala-AIB-dSer-Tyr-Gln-Cys;

a sequence identical to Cys-Ala-AIB-dSer-Tyr-Gln-Cys except for one or more conservative substitutions of amino acids in said Cys-Ala-AIB-dSer-Tyr-Gln-Cys sequence;

a sequence identical to Cys-Ala-AIB-Ser-dTvr-Gln-Cys except for one or more conservative substitutions of amino acids in said Cys-Ala-AIB-Ser-dTyr-Gln-Cys sequence;

wherein said TNFα antagonist has a restricted conformation, and bind to TNF p55 receptor and/or TNF p75 receptor.

16. A peptide having the amino acid sequence Cys-Ala-Arg-Asp-Asn-Gln-Ala-Cys SEQ ID NO:1.

17. A peptide having the amino acid sequence Cys-Arg-Arg-Ala-Asn-Ala-dCys.

18. A TNFα antagonist having the formula: Cys-Glu-AIB-Glu-Cys SEQ ID NO:6, Pen-Glu-AIB-Glu-Pen SEQ ID NO:7, Cys-Glu-Gly-Ala-Glu-Cys SEQ ID NO:8, Pen-Glu-Gly-Ala-Glu-Pen SEQ ID NO:9, Cys-Pro-Arg-Glu-Thr-Pro-Glu-Gly-Ala-Glu-Ala-Lys-Pro-Cys SEQ ID NO:10, Cys-Pro-Glu-Thr-Pro-Glu-Gly-Ala-Glu-Ala-Lys-Pro-Cys SEQ ID NO:11 or Pen-Thr-Pro-Glu-Gly-Ala-Glu-Ala-Pen SEQ ID NO:12;

wherein said TNFα antagonist has a restricted conformation, and bind to TNF p55 receptor and/or TNF p75 receptor.

19. The compound of claim 18 wherein said compound is Cys-Glu-AIB-Glu-Cys SEQ ID NO:6.

20. The compound of claim 18 wherein said compound is Pen-Glu-AIB-Glu-Pen SEQ ID NO:7.

21. The compound of claim 18 wherein said compound is Cys-Glu-Gly-Ala-Glu-Cys SEQ ID NO:8.

22. The compound of claim 18 wherein said compound is Pen-Glu-Gly-Ala-Glu-Pen SEQ ID NO:9.

23. The compound of claim 18 wherein said compound is Cys-Pro-Arg-Glu-Thr-Pro-Glu-Gly-Ala-Glu-Ala-Lys-Pro-Cys SEQ ID NO:10.

24. The compound of claim 18 wherein said compound is Cys-Pro-Glu-Thr-Pro-Glu-Gly-Ala-Glu-Ala-Lys-Pro-Cys SEQ ID NO:11.

25. The compound of claim 18 wherein said compound is Pen-Thr-Pro-Glu-Gly-Ala-Glu-Ala-Pen SEQ ID NO:12.

26. The compound of claim 15 wherein said compound is Cys-Ala-AIB-dSer-Tyr-Gln-Cys.

27. The compound of claim 15 wherein said compound is Cys-Ala-AIB-Ser-dTyr-Gln-Cys.

28. The compound of claim 2 wherein $R_3$ is Glu.

29. The compound of claim 2 wherein $R_4$ is amino isobutyric acid (AIB), Gly-Ala, Gly-Gly, Ala-Gly, or Ala-Ala.

30. The compound of claim 2 wherein $R_5$ is Glu.

31. The compound of claim 3 wherein $R_3$ is Glu.

32. The compound of claim 3 wherein $R_5$ is Glu.

33. The compound of claim 4 wherein $R_3$ is Glu.

34. The compound of claim 4 wherein $R_4$ is amino isobutyric acid (AIB), Gly-Ala, Gly-Gly, Ala-Gly, or Ala-Ala.

35. The compound of claim 4 wherein $R_5$ is Glu.

* * * * *

UNITED STATES PATENT AND TRADEMARK OFFICE
CERTIFICATE OF CORRECTION

PATENT NO. : 6,107,273
DATED : August 22, 2000
INVENTOR(S) : Bradford A. Jameson It is certified that error appears in the above-identified patent and that said Letters Patent is hereby corrected as shown below:

Col. 5, line 59, after "TNFα" there should be a space separating the next word "inhibitors".

Col. 8, line 65, "ss" should be –less–

Col. 9, line 17, "molecuile" should be –molecule–.

Col. 12, line 44, "after "TNFα" there should be a space separating the next word "cytotoxity"

Signed and Sealed this

Twenty-fourth Day of April, 2001

*Attest:*

NICHOLAS P. GODICI

*Attesting Officer*   Acting Director of the United States Patent and Trademark Office